United States Patent [19]

Tanaka et al.

[11] Patent Number: 4,702,998
[45] Date of Patent: Oct. 27, 1987

[54] PROCESSING SOLUTION FOR LIGHT-SENSITIVE SILVER HALIDE PHOTOGRAPHIC MATERIAL COMPRISES METAL COMPLEXES OF LARGE POLYAMINE DERIVATIVES

[75] Inventors: M. Tanaka, Nagoya; Kazuhiro Kobayashi; Shigeharu Koboshi, both of Tokyo, all of Japan

[73] Assignee: Konishiroku Photo Industry Co., Ltd., Tokyo, Japan

[21] Appl. No.: 843,181

[22] Filed: Mar. 24, 1986

[30] Foreign Application Priority Data

Mar. 30, 1985 [JP] Japan .................................. 60-67844

[51] Int. Cl.$^4$ .......................... G03C 5/44; G03C 7/30
[52] U.S. Cl. .................... 430/430; 252/186.1; 430/447; 430/461; 540/452; 540/454; 540/460; 540/474; 540/554
[58] Field of Search .................. 430/430, 461, 447; 540/554, 474, 460, 452, 454; 252/186.1

[56] References Cited

U.S. PATENT DOCUMENTS

| | | |
|---|---|---|
| 3,860,576 | 1/1975 | Ham et al. ............................ 540/474 |
| 3,977,981 | 8/1976 | Dunlop et al. ....................... 540/474 |
| 4,001,212 | 1/1977 | Richman .............................. 540/474 |
| 4,168,265 | 9/1979 | Tabushi et al. ..................... 540/474 |
| 4,174,319 | 11/1979 | Kobuke ................................ 540/474 |
| 4,174,428 | 11/1979 | Tabushi et al. ................. 540/474 V |
| 4,578,517 | 3/1986 | Johnson et al. ................. 540/474 X |

FOREIGN PATENT DOCUMENTS

| | | | |
|---|---|---|---|
| 0130593 | 10/1979 | Japan ................................... | 540/476 |
| 0168245 | 10/1982 | Japan ................................... | 540/474 |
| 1529150 | 10/1978 | United Kingdom ................ | 540/474 |
| 1081169 | 3/1984 | U.S.S.R. ............................. | 540/474 |

OTHER PUBLICATIONS

Stetter et al., "Daystelling und Komplexbildung von Polyazacycloalkan-N-Essigsauren", Tetrahedran, vol. 37, pp. 767 to 772.

*Primary Examiner*—John E. Kittle
*Assistant Examiner*—Mukund J. Shah
*Attorney, Agent, or Firm*—Frishauf, Holtz, Goodman & Woodward

[57] ABSTRACT

There are disclosed a processing solution having bleaching ability for use in light-sensitive silver halide photographic material, which comprises at least one selected from metal complexes of large cyclic polyamine derivatives and a method for processing of light-sensitive silver halide photographic material, which comprises carrying out development processing of an exposed light-sensitive silver halide photographic material and then processing the developed material with the processing solution.

The processing solution of the present invention has potent bleaching power, and can afford excellent photographic image characteristics by processing therewith.

14 Claims, No Drawings

PROCESSING SOLUTION FOR LIGHT-SENSITIVE SILVER HALIDE PHOTOGRAPHIC MATERIAL COMPRISES METAL COMPLEXES OF LARGE POLYAMINE DERIVATIVES

BACKGROUND OF THE INVENTION

This invention relates to a processing solution for photographic material and its processing method, particularly to a processing solution to be used for bleaching of image silver in processing of a light-sensitive silver halide photographic material and its processing method.

Bleaching solution, bleach-fixing solution and reducer have been known as a processing solution for photographic material having bleaching ability.

Among them, this kind of processing solution in processing of a light-sensitive silver halide photographic material employes widely an inorganic oxidizing agent such as red prussiate, bichromate, etc. as the oxidizing agent for bleaching image silver.

However, some serious drawbacks have been pointed out for the processing solutions having bleaching ability containing these inorganic oxidizing agents. For example, red prussiate and bichromate are relative excellent in bleaching power of image silver, but there is a fear of generation of cyanide ions or hexavalent chromium ions harmful to human bodies, thus having undesirable properties in prevention of pollution. Also, since these oxidizing agents have very strong oxidizing power and oxidize the solubilizing agent for silver halide such as thiosulfates, they can hardly be permitted to co-exist in the same processing solution. Thus, it is almost impossible to use these oxidizing agents in a bleach-fixing bath, whereby the object of making processing quick and simple can hardly be accomplished. Further, the processing solution containing these inorganic oxidizing agents has the drawback that the waste solution can be regenerated without being discarded with difficulty.

In contrast, recently, processing solutions employing an organic metal chelate compound such as aminopolycarboxylic acid metal complex have been used widely as the processing solution which is free from the problems in pollution and can meet the requirements of speed-up and simplification of processing as well as regenerability of waste solution.

As the aminopolycarboxylic acid metal complex to be used as the oxidizing agent, iron, copper and cobalt complexes of ethylenediaminetetraacetic acid, nitrilotriacetic acid, hydroxyalkylethylenediamine, diethylenetriaminepentaacetic acid and the like have been known. However, the processing solutions employing these aminopolycarboxylic acid metal complexes, due to slow oxidizing power, are delayed in bleaching speed (oxidation speed) of the image silver (metal silver) formed in the developing step, and therefore are not suited for the object of quick processing. Of these processing solutions, the processing solution employing iron salt of ethylenediaminetetraacetic acid (hereinafter called EDTA iron complex) is considered to be superior to other aminopolycarboxylic acid metal complexes with respect to bleaching power, and practically applied in a part of the business, but it is still inferior in bleaching power than the red prussiate type bleaching solution which has been used in the prior art. Accordingly, efforts have been made to use a bleaching accelerator, but no satisfactory result has not yet been obtained. Also, aminopolycarboxylic acid metal complexes other than the EDTA iron complex are weak in bleaching power, and when these are to be applied for processing solutions having bleaching ability, the concentration of said aminopolycarboxylic acid metal complexes is required to made higher, which is limited in economy and solubility. Thus, it has been considered that practical application of them is almost impossible. Further, in the bleach-fixing solution employing the aminopolycarboxylic acid metal complex of the prior art, when carrying out bleach-fixing processing immediately after the step containing a reducing agent such as color developer, etc., the reducing agent will be brought about into the bleach-fixing bath, or the aminopolycarboxylic acid metal complex will be reduced by the reducing agent in the bleach-fixing solution, whereby the reduced product of the aminopolycarboxylic acid metal complex reduces the color forming dye, particularly cyan dye, to the leuco form. As a result, the dye image becomes tinted in red, or contamination or stain occurs on the processed image surface due to lowering in bleaching power of the aminopolycarboxylic acid metal complex, whereby no stisfactory color reproduction can disadvantageously be obtained.

Further, in the bleach-fixing solution employing an aminopolycarboxylic acid metal complex of the prior art, there is the drawback that the sulfite ion used as the preservative disappears by oxidation over prolonged storage, whereby thiosulfate ions used as the fixing agent may be oxidized to generate sulfur or silver sulfate. Furthermore, when bleaching or bleach-fixing processing is performed immediately after the color developing processing for shortening of the processing time, the color developing solution is brought about by the light-sensitive material into the bleaching bath or bleach-fixing bath, whereby there is involved the drawback that the color developing agent is liable to be oxidized by the bleaching agent to generate tar.

SUMMARY OF THE INVENTION

Accordingly, the present invention has been accomplished in view of the state of the art as described above, and an object of the present invention is to provide a processing solution having potent bleaching power, which can afford excellent photographic image characteristics by processing therewith.

Also, another object of the present invention is to provide a processing solution, which can give a dye image satisfactorily color developed without turbidity in color and generation of stain, etc. to the light-sensitive material after processing, in processing of a light-sensitive silver halide photographic material.

Further, still another object of the present invention is to provide a processing solution which is excellent in storage stability and free from generation of tar.

Further, still another object of the present invention is to provide a processing solution which is harmless to human bodies with little problem in pollution, and which can be used after regeneration.

According to the present invention, a processing solution having epoch-making performance having a bleaching power which is superior to red prussiate or EDTA-iron complex, while employing a non-pollutative and safe oxidizing agent other than metal complexes of aminopolycarboxylic acids conventionally used in the prior art such as EDTA-iron complex and the like, can be obtained and an excellent color image free from the drawbacks as mentioned above can be obtained by use thereof.

The above objects of the present invention can be accomplished by a processing solution having bleaching ability for use in light-sensitive silver halide photographic material, which comprises containing at least one selected from metal complexes of large cyclic polyamine derivatives and a processing method by use thereof.

PREFERRED EMBODIMENTS OF THE INVENTION

The large cyclic polyamine constituting the metal complex of large polyamine derivative to be used in the present invention is a compound in which at least three nitrogen atoms are linked through at least two carbon atoms to form a ring, and the above-mentioned at least three nitrogen atoms may also be linked through atoms other than the above carbon atoms, for example, oxygen atoms. Here, the large cyclic polyamine refers to one having at least 3 nitrogen atoms for forming the above ring, with the sum of the atoms for forming the ring being at least 9. Also, the above carbon atom may have substituents. Preferable substituents include an alkyl group, a hydroxy group, an amino group and others.

The above alkyl group may preferably be an alkyl group having carbon atoms of not more than 6, such as methyl, ethyl, propyl and the like, and this alkyl group may have substituents such as a hydroxy group, an amino group or the like. Specific examples are hydroxyalkyl groups, preferably hydroxyalkyl groups having not more than 6 carbon atoms such as a hydroxymethyl group, a hydroxyethyl group or the like, aminoalkyl groups, preferably aminoalkyl groups having not more than 6 carbon atoms such as an aminomethyl group, an aminoethyl group or the like. Further, the above amino group may have substituents, including, for example, alkyl groups having preferably not more than 6 carbon atoms such as methyl, ethyl, propyl or the like.

The linking group for forming the metal complex of a large cyclic polyamine derivative of the present invention through linking of at least 3 nitrogen atoms may include the following groups:

 (a) —CH₂CH₂—

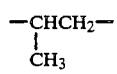 (b) —CHCH₂—
                          |
                          CH₃

 (c) —CH₂CH₂CH₂—

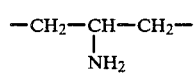 (d) —CH₂—CH—CH₂—
                              |
                              NH₂

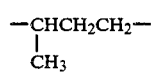 (e) —CHCH₂CH₂—
                         |
                         CH₃

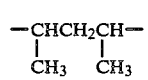 (f) —CHCH₂CH—
                         |      |
                         CH₃   CH₃

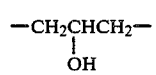 (g) —CH₂CHCH₂—
                              |
                              OH

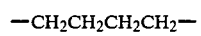 (h) —CH₂CH₂CH₂CH₂—

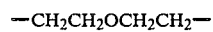 (i) —CH₂CH₂OCH₂CH₂—

The above linking groups constituting the large cyclic polyamine metal complex may be all the same or different in the same molecule, and also two or more kinds may be available.

Preferable compounds of these large cyclic polyamine derivatives may include those shown by the following formula (I) to (XVI):

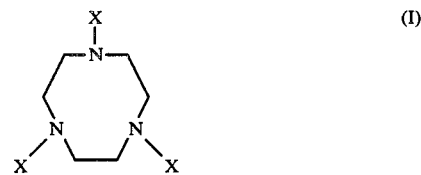 (I)

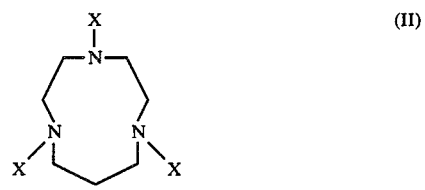 (II)

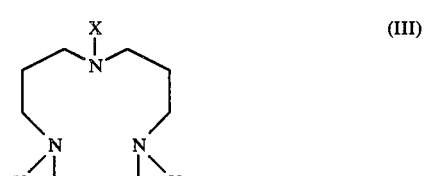 (III)

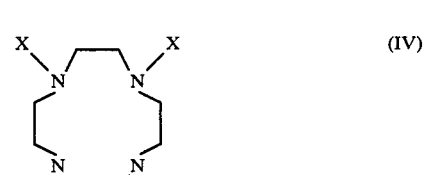 (IV)

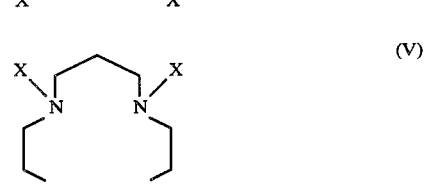 (V)

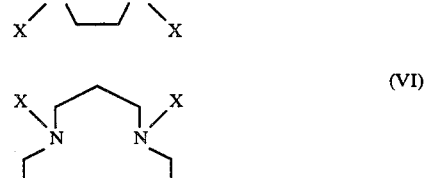 (VI)

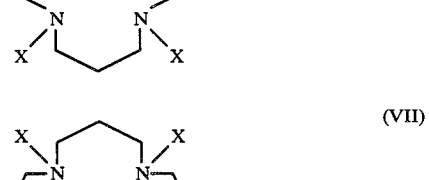 (VII)

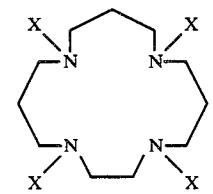

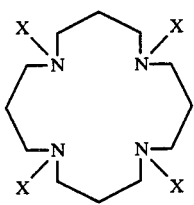 (VIII)

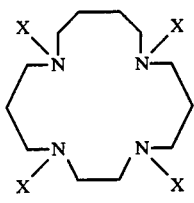 (IX)

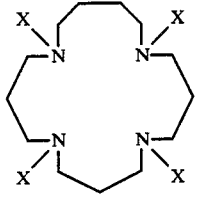 (X)

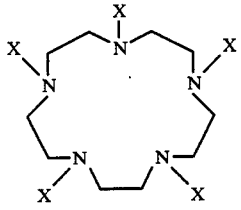 (XI)

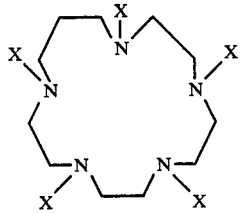 (XII)

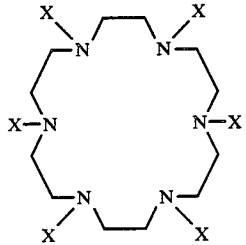 (XIII)

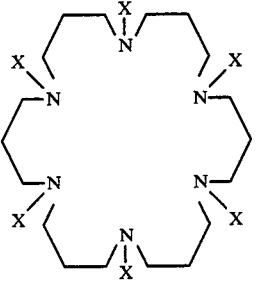 (XIV)

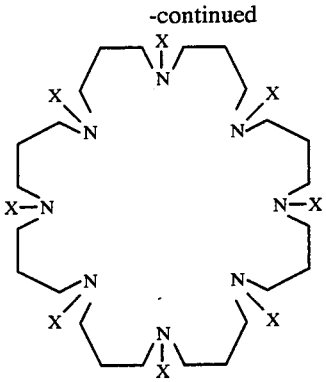 (XV)

and

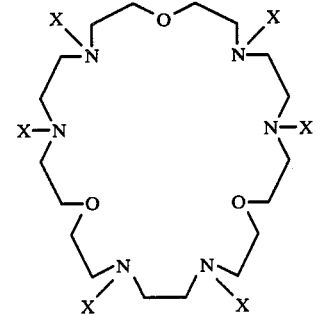 (XVI)

For example, the compound of the formula (I) shows a compound in which three nitrogen atoms are linked with the above linking group (a).

X shown in each of the compounds of the above formulae (I) to (XVI) represents a hydrogen atom, a carboxymethyl group or a phosphonomethyl group. More specifically, there may be included the case in which all are carboxymethyl groups, the case in which at least one is carboxymethyl group and the others are hydrogen atoms, the case in which all are phosphonomethyl groups, the case in which at least one is phosphonomethyl group and the others are carboxymethyl groups, the case in which at least one is carboxymethyl group, at least one of the others is phosphonomethyl group and the remainder are hydrogen atoms, and the case in which at least one is phosphonomethyl group and the others are hydrogen atoms.

In the present invention, the compounds of the formulae (I) to (XVI) are preferably those when all X's are carboxymethyl groups or phosphonomethyl groups.

Of the compounds represented by the above formulae (I) to (XVI), particularly preferred are the compounds shown below.

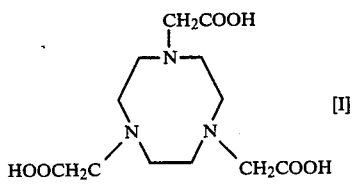 (A-1)

-continued
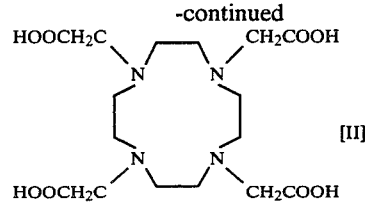
(A-2) [II]
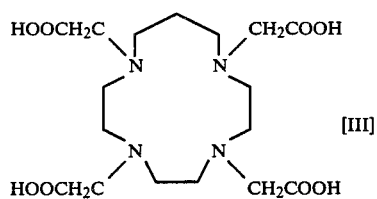
(A-3) [III]
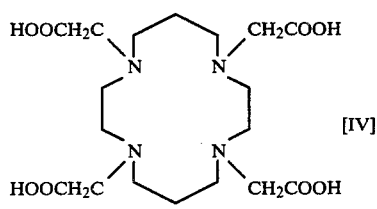
(A-4) [IV]
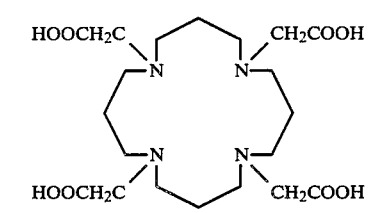
(A-5)
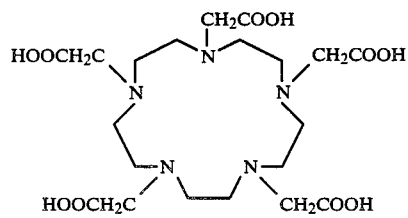
(A-6)
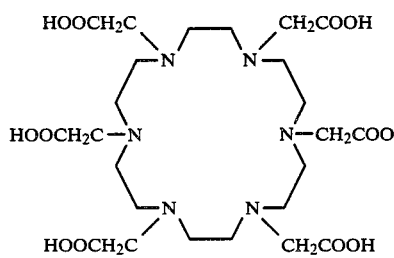
(A-7)
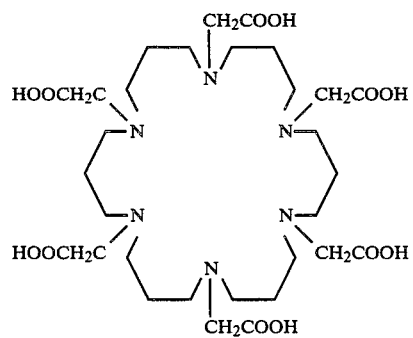
(A-8)
-continued
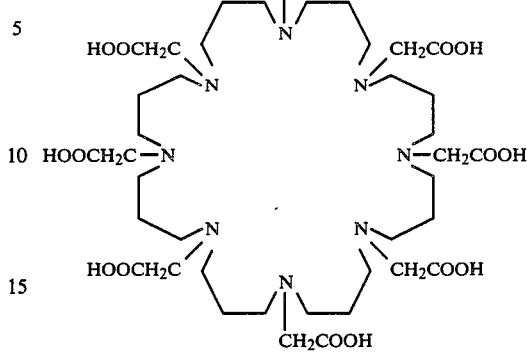
(A-9)
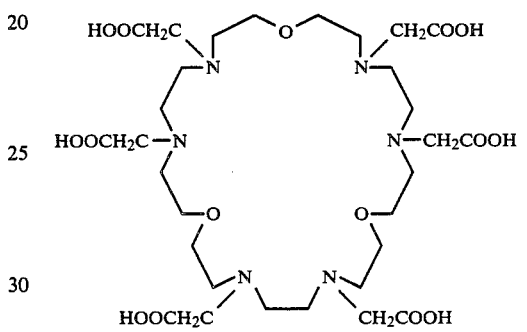
(A-10)
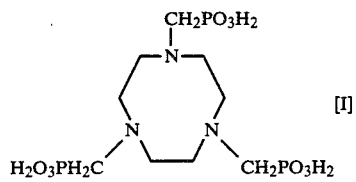
(B-1) [I]
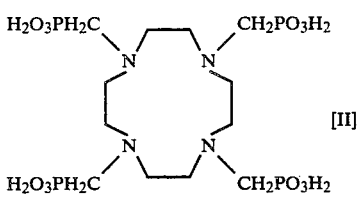
(B-2) [II]
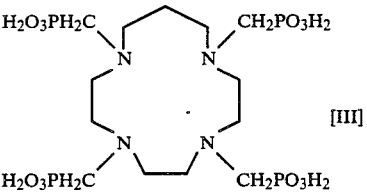
(B-3) [III]
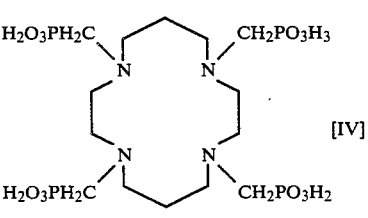
(B-4) [IV]

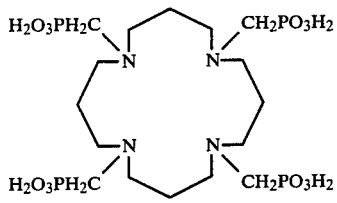 (B-5)

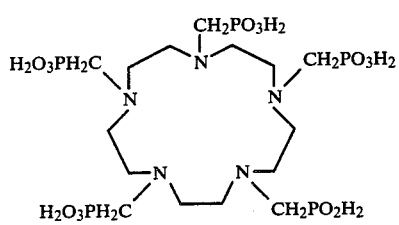 (B-6)

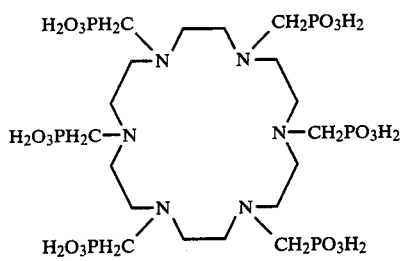 (B-7)

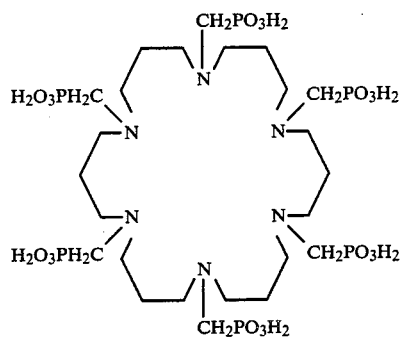 (B-8)

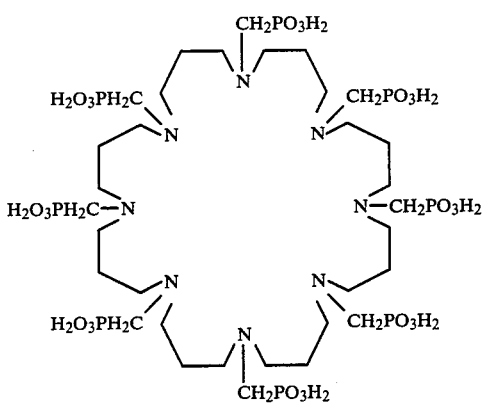 (B-9)

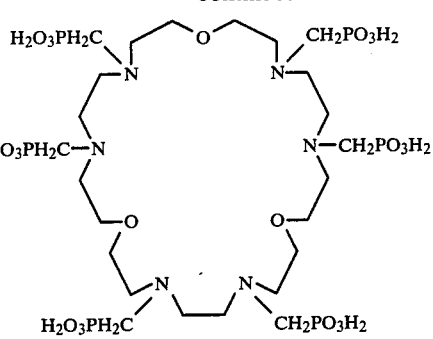 (B-10)

These compounds can be synthesized according to the synthetic methods in general as described in, for example, Journal of Chemical Society of Japan, 1975, p. 1182; Tetrahedron, Vol. 37, p. 767. 1981. For example, the compound of (A-1) can be synthesized as follows.

SYNTHESIS EXAMPLE [Compound of (A-1)]

In an aqueous solution containing diethylenetriamine and 3-fold moles of sodium hydroxide, an aqueous solution having 3-fold moles of p-toluenesulfonic acid chloride dissolved in ether is gradually added. After the mixture is stirred at room temperature for one hour, the formed white precipitate is filtered, washed with water and then recrystallized from methanol to give N,N',N''-tri-(p-toluene sulfonic acid)-diethylenetriamine as colorless needle-like crystals. Subsequently, anhydrous potassium carbonate is added to dimethylformamide, and the resulting mixture under slowly stirring while maintained at 120° C., is added into a solution having N,N',N''-tri-(p-toluene sulfonic acid)-diethylenetriamine and equal mole of 1,3-dibromopropane dissolved in dimethylformamide by means of a dropping device of Hershberg at the rate of one drop per 10 seconds over 30 to 40 hours. The mixture is further stirring at 115° to 120° C. for 7 hours, then cooled to room temperature and filtered. The filtrates is concentrated to 1/10, followed by addition of water to effect precipitation, and the precipitate is extracted with hot benzene. The extracted benzene is dried over anhydrous sodium sulfate and then removed to give a viscous yellowish brown oil. This is dissolved in ethanol and left to stand. The resulting crystal is recrystallized from ethanol-benzene to obtain 1,4,7-triazacyclononane-N,N',N''-tri-(p-toluene sulfonic acid) as colorless needle-like crystals. This is refluxed with 70% sulfuric acid for 48 hours to be hydrolyzed, diluted with water and added with ethanol to obtain crystals. The crystals are dissolved in an aqueous strong alkali solution, extracted with cyclohexane, the solvent is evaporated, and the residue is distilled under reduced pressure to obtain crystals. Recrystallization of the crystals from water-ethanol gives 1,4,7-triazacyclononane trihydrochloride. This is dissolved in water, added with 3-fold mole of chloroacetic acid and then neutralized with lithium hydroxide. While raising gradually the temperature, a lithium hydroxide solution is added dropwise so as to maintain pH at 9. After heating is continued until the alkali becomes not consumed completely, pH is adjusted to 2 with hydrochloric acid, and most of water is evaporated, followed by addition of ethanol, to obtain crystals. Recrystallization of the crystals from water-ethanol gives 1,4,7-triazacyclononane-N,N',N''-triacetic acid (A-1). This compound is confirmed by elemental analysis and IR-absorption spectrum.

Other large cyclic polyamine derivatives having carboxymethyl groups can also be synthesized from respective corresponding straight chain polyamines according to similar methods.

On the other hand, large cyclic polyamine derivatives having phosphonomethyl groups can be also synthesized in substantially the same manner as large cyclic polyamine derivatives having carboxymethyl groups by use of chloromethylenephosphonic acid in place of chloroacetic acid.

The metal atom as the center atom constituting the metal complex with the compound represented by the above formula according to the present invention may preferably be iron, but copper, cobalt and others can also be used.

The amount of the large cyclic polyamine derivative metal complex of the present invention to be used in preparation of the processing solution according to the present invention may differ depending on the kind of the complex and the kind of the processing solution, but it is generally used in an amount within the range of from 3 g to 350 g per liter of the processing solution.

The processing solution having bleaching ability to be used in the present invention refers specifically to a bleaching solution, bleach-fixing solution and reducer.

The metal in the large cyclic polyamine derivative metal complex of the present invention is a metal which can be coordination bonded to the large cyclic polyamine derivative, such as iron, cobalt, copper and others. The large cyclic polyamine derivative metal complex particularly preferred in the present invention is a metal salt of higher valence, for example, ferric salt.

The light-sensitive silver halide color photographic material to be used in the present invention generally has dye image forming constituent units having light sensitivities to the three primary color regions of the spectrum, and each constituent unit can comprise a monolayer emulsion layer or a multilayer emulsion layer having sensitivity to a certain region of the spectrum (in this case, sensitivities of the respective emulsion layers should preferably be different). Also, it can also have layers such as filter layer, intermediate protective layer, subbing layer and others. Including the layers of the image forming constituent units, the layers of the photosensitive material can be provided by coating in various orders as known in this field of the art.

A typical color light-sensitive material comprises a cyan dye image forming constituent unit comprising at least one red-sensitive silver halide emulsion layer having at least one cyan dye forming coupler, a magenta dye image forming constituent unit comprising at least one green-sensitive silver halide emulsion layer having at least one magenta dye forming coupler and a yellow dye image forming constituent unit comprising at least one blue-sensitive silver halide emulsion layer having at least one yellow dye forming coupler together with non-sensitive layers provided by coating on a support.

The color light-sensitive material can use open-chain ketomethylene type couplers used in this field of the art as the yellow color forming coupler. Examples of usable yellow color forming couplers include those as disclosed in U.S. Pat. No. 2,875,057, No. 3,265,506, No. 3,408,194, No. 3,551,155, No. 3,582,322, No. 3,725,072 and No. 3,891,445; West German Pat. No. 1,547,868; and West Germam Patent Applications (OLS) No. 2,213,461, No. 2,219,917, No. 2,261,361, No. 2,414,006 and 2,263,875.

Examples of the magenta color forming coupler include those as disclosed in U.S. Pat. No. 2,600,788, No. 2,983,608, No. 3,062,653, No. 3,127,269, No. 3,311,476, No. 3,419,391, No. 3,519,429, No. 3,558,319, No. 3,582,322, No. 3,615,506, No. 3,834,908 and No. 3,891,445; West German Pat. No. 1,810,464; West German Patent Applications (OLS) No. 2,408,665, No. 2,417,945, No. 2,418,959 and No. 2,424,467; and Japanese Patent Publication No. 6031/1965.

Phenol type compounds and naphthol type compounds can be used as the cyan color forming coupler. Its examples include those as disclosed in U.S. Pat. No. 2,369,929, No. 2,434,272, No. 2,474,293, No. 2,521,908, No. 2,895,826, No. 3,034,892, No. 3,311,476, No. 3,458,315, No. 3,476,563, No. 3,583,971, No. 3,591,383 and No. 3,767,411; West German Patent Applications (OLS) No. 2,414,830 and No. 2,454,329; and Japanese Provisional Patent Publication No. 59838/1973.

As the colored coupler, there may be employed those as disclosed in U.S. Pat. No. 3,476,560, No. 2,521,908 and No. 3,034,892; Japanese Patent Publications No. 2016/1969, No. 22335/1963, No. 11304/1967 and No. 32461/1969; and West German Patent Application (OLS) No. 2,418,959.

Also, for improvemeht of photographic characteristics, a non-coloration dye called as competing coupler can be also contained.

Further, it is also possible to use a developing inhibitor releasing compound (hereinafter called DIR compound). Examples of the DIR compound may include those as disclosed in U.S. Pat. No. 3,148,062, No. 3,227,554; U.K. Patent No. 2,010,818; Japanese Provisional Patent Publications No. 69624/1977, No. 135835/1980 and No. 44831/1982.

For introduction of couplers and DIR compound into silver halide emulsion layer, any desired method used in this field of the art, for example, the method as disclosed in U.S. Pat. No. 2,322,027 may be used.

In the light-sensitive silver halide color photographic material of the present invention, the silver halide to be used in the silver halide emulsion may include any of those conventionally used in silver halide photographic emulsions such as silver bromide, silver chloride, silver iodobromide, silver chlorobromide, silver chloroiodobromide and the like.

The above silver halide emulsion can be chemically sensitized with a chemical sensitizer such as noble metal sensitizer, sulfur sensitizer, selenium sensitizer and a reducing sensitizer.

Further, the silver halide emulsion can also be subjected if necessary to intensifying sensitization by spectral sensitization by use of a cyanine dye such as cyanine, merocyanine, carbocyanine and the like, alone or in combination, or a combination thereof with a styryl dye.

Its choice can be determined as desired depending on the purpose and use of the light-sensitive silver halide color photographic material such as wavelength region to be sensitized, sensitivity and others.

It is further possible to add additives conventionally used in the field of photography such as stabilizers, film hardeners and surfactants in the above silver halide emulsion.

The processing solution having bleaching ability of the present invention is particularly effective for processing of light-sensitive silver halide color photographic materials such as color paper, color reversal, color negative, color print film or the like. It is also effectively applicable as a reducer for monochromatic light-sensitive silver halide photographic materials. For example, as a reducer for light-sensitive silver halide photographic materials for use in printing plate, Farmer reducer, persulfate reducer, permanganate reducer, ethylenediaminetetraacetic acid metal complex reducer and others have been employed. Farmer reducer and permanganate reducer contain harmful substances such as cyan and manganese, respectively, and persulfate reducer is rapidly deteriorated in oxidizing ability with the lapse of time. Ethylenediaminetetraacetic acid metal complex reducer has no such drawbacks, but slow in oxidizing power. This drawback can be solved by use of a large cyclic polyamine derivative metal complex as the reducer in place of iron salt of ethylenediaminetetraacetic acid.

Processing by the processing solution having bleaching ability comprising a large cyclic polyamine derivative metal complex added therein may be carried out at any time in the processing steps, provided that the processing step of oxidative bleaching of image silver after developing processing is included. In processing of the light-sensitive silver halide color photographic material, a pre-film-hardening neutralization bath may be included in the processing step, or alternatively a stopping bath or a stopping fixing bath may be included, or further processing may be performed from developing step directly to bleaching or bleach-fixing step.

The processing steps to be used in the present invention are series of continuous processing steps as shown by the following examples:

(1) Color developing processing→Bleach-fixing processing→Water washing→Stabilizing;

(2) Color developing processing→Bleaching processing→Water washing→Fixing processing→Water washing→Stabilizing;

(3) Color developing processing→Bleaching processing→Fixing processing→Water washing→Stabilizing;

(4) Monochromatic developing processing→Reversal exposure→Color developing processing→Bleach-fixing processing→Water washing→Stabilizing;

(5) Monochromatic processing→Stopping→Color developing processing containing foggant→Bleaching processing→Fixing processing→Water washing→Stabilizing.

The processing temperature in the method for processing of the light-sensitive silver halide color photographic material is set within a preferable range depending on the light-sensitive material and the processing recipe. In general it is from 20° to 60° C., but the light-sensitive silver halide color photographic material is suitable particularly for processing at 30° C. or higher.

The color developing agent to be used in the color developing solution is inclusive of known compounds which are utilized widely in various color photographic processes. Particularly useful color developing agents are aromatic primary amine type color developing agents. Among them, particularly useful compounds include N,N-diethyl-p-phenylenediamine hydrochloride, N-methyl-p-phenylenediamine hydrochloride, N,N-dmethyl-p-phenylenediamine hydrochloride, 2-amino-5-(N-ethyl-N-dodecylamino)-toluene, N-ethyl-N-β-methanesulfonamidoethyl-3-methyl-4-aminoaniline sulfate, N-ethyl-N-β-hydroxyethylaminoaniline sulfate, 4-amino-3-methyl-N,N-diethylaniline hydrochloride, N-ethyl-N-β-hydroxyethyl-3-methyl-4-aminoaniline sulfate, 4-amino-N-(β-methoxyethyl)-N-ethyl-3-methylaniline-p-toluene sulfonate and the like.

These color developing agents may be contained as the color developing agent itself or as a precursor thereof previously in the light-sensitive silver halide color photographic material.

These aromatic primary amine type color developing agents are required to be added in an amount which can give sufficient color formation during color developing processing. This amount may differ considerably depending on the light-sensitive silver halide color photographic material employed and others, but it is approximately from 0.1 mole to 5 moles, preferably from 0.5 mole to 3 moles, per mole of the light-sensitive silver halide. These color developing agents can be used either singly or in combination.

The color developing solution to be used in the present invention may also contain, in addition to the above aromatic primary amine type color developing agent, alkali agents such as sodium hydroxide, potassium hydroxide, potassium carbonate, trisodium phosphate and others; pH buffers such as boric acid, acetic acid and others; known development accelerators such as thioethers, 1-aryl-3-pyrazolidones, N-methyl-p-aminophenols, polyalkylene glycols and others; various organic solvents such as benzyl alcohol, ethanol, butanol, ethylene glycol, diethylene glycol, acetone, N,N-dimethylformamide and others; developing inhibitors such as potassium bromide, nitrobenzimidazole and others; preservatives such as sulfites, hydroxylamine, glucose, alkanol, amines and others; hard water softeners such as polyphosphoric acid compounds, nitrilotriacetic acid and others.

The color developing solution to be used in the present invention has a pH value which is generally 7.0 or higher, preferably about 9.5 to 13.0.

The temperature in the color developing processing to be used in the present invention may preferably be 30° to 60° C., and the developing time preferably 30 seconds to 10 minutes.

In the processing solution of the present invention, when a bleaching solution containing the large cyclic polyamine derivative metal complex of the present invention for bleaching processing, generally fixing processing practiced to perform subsequently. Also, when a bleach-fixing solution containing the above complex is used, bleaching processing and fixing processing are conducted simultaneously in the same solution. The bleaching agent to be used in the above bleaching solution or bleach-fixing solution may include, in addition to the large cyclic polyamine derivative metal complexes of the present invention, aminopolycarboxylic acid metal complexes, aliphatic polycarboxylic acid metal complexes and persulfates.

The aminopolycarboxylic acid forming the above-mentioned aminopolycarboxylic acid metal complex may include the following:

Ethylenediaminetetraacetic acid;
Diethylenetriaminepentaacetic acid;
Ethylenediamine-N-(β-hydroxyethyl)-N,N',N'-triacetic acid;
Propylenediaminetetraacetic acid;
Nitrilotriacetic acid;
Cyclohexanediaminetetraacetic acid;
Iminodiacetic acid;
Methyliminodiacetic acid;

Ethyliminodiacetic acid;
Hydroxyethyliminodiacetic acid;
Hydroxylmethyliminodiacetic acid;
Propyliminodiacetic acid;
Butyliminodiacetic acid;
Dihydroxyethylglycine;
Ethyletherdiaminetetraacetic acid;
Glycoletherdiaminetetraacetic acid;
Ethylenediaminetetrapropionic acid;
Phenylenediaminetetraacetic acid;
Disodium ethylenediaminetetraacetate;
Tetra(trimethylammonium)ethylenediaminetetraacetate;
Tetrasodium ethylenediaminetetraacetate;
Pentasodium diethylenetriaminepentaacetate;
Sodium ethylenediamine-N-($\beta$-hydroxyethyl)-N,N',N'-triacetate;
Sodium propylenediaminetetraacetate;
Sodium nitrilotriacetate;
Sodium cyclohexanediaminetetraacetate.

The metal which forms a complex with the above aminopolycarboxylic acid may be, for example, iron, cobalt, copper and others. Particularly preferable metal complex of aminopolycarboxylic acid is metal salt of higher valence, for example, a ferric salt.

The amount of these aminopolycarboxylic acid metal complex used may preferably be within the range of from 0.01 to 0.4 mole per liter of the processing solution.

The bleaching solution or the bleach-fixing solution of the present invention may further contain a chelating agent such as a large cyclic polyamine derivative not forming a complex with a metal atom or the polycarboxylic acids, etc. as exemplified above. The amount of these chelating agents used may preferably be within the range of from 0.1 g to 100 g per liter of the processing solution.

When the processing solution is a bleaching solution in the present invention, it can also contain various additives together with the large cyclic polyamine derivative metal complex of the present invention as described above. As the additive, it is particularly desirable to contain a rehalogenating agent such as alkali halides or ammonium halides, including potassium bromide, sodium bromide, sodium chloride, ammonium bromide or the like. Also, there may suitably be added those conventionally known to be added into bleaching solutions, for example, pH buffers such as borates, oxalates, acetates, carbonates, phosphates and others, solubilizing agent such as triethanolamine and others, aminopolycarboxylic acid or salts thereof, alkylamines, polyethyleneoxides and so on.

When the processing solution is a bleach-fixing solution in the present invention, it is possible to use a silver halide fixing agent such as thiosulfates, thiocyanates, thioureas and others together with the large cyclic polyamine derivative metal complex of the present invention. Also, a bleach-fixing solution comprising a composition in which a small amount of a halogen compound such as potassium bromide is added, or a bleach-fixing solution comprising a composition in which on the contrary a large amount of a halogen compound which as potassium bromide is added can be used.

As the above halogen compound, other than potassium bromide, hydrochloric acid, hydrobromic acid, lithium bromide, sodium bromide, ammonium bromide, potassium iodide, ammonium iodide and the like can be used.

As the silver halide fixing agent to be contained in the bleach-fixing solution, there may be employed compounds capable of forming water-soluble complexes through the reaction with silver halide used in conventional fixing processing, for example, thiosulfates such as potassium thiosulfate, sodium thiosulfate, ammonium thiosulfate; thiocyanates such as potassium thiocyanate, sodium thiocyanate, ammonium thiocyanate; or thioureas, thioether, highly concentrated bromides, iodides and the like.

In the bleach-fixing solution, similarly as in the case of bleaching solution, it is possible to incorporate pH buffers comprising various salts of boric acid, borax, sodium hydroxide, potassium hydroxide, sodium carbonate, potassium carbonate, sodium bicarobnate, potassium bicarbonate, acetic acid, sodium acetate, ammonium hydroxide and the like, either alone or as a combination of two or more compounds. Furthermore, various fluorescent brighteners, defoaming agents or surfactants can also be contained.

It is also possible to incorporate suitably preservatives such as hydroxylamine, hydrazine, sulfite, isomeric metabisulfite, bisulfite adducts of aldehyde or ketone compounds, etc; organic chelatign agent such as aminopolycarboxylic acid, etc.; a kind of stabilizer such as nitroalcohol nitrate, etc.; solubilizing agents such as alkanolamine, etc.; antistain agents such as organic amines, etc.; organic solvent such as methanol, N,N-dimethylformamide, N,N-dimethylsulfoxide, etc.

Further, in carrying out automatic developing processing, a supplemental solution is supplemented by an automatic supplementing system into a bleaching solution or bleach-fixing solution. That is, the components in the bleaching solution or bleach-fixing solution consumed corresponding to the processed amount of the light-sensitive silver halide color photographic material are supplemented, or necessary components are supplemented to compensate for dilution effected by the solution brought about from the color developing processing or water washing processing or to compensate for the components brought out by the light-sensitive silver halide photographic material from the bleaching solution or the bleach-fixing solution. Accordingly, the supplemental solution is ordinarily more concentrated than the bleaching solution or bleach-fixing solution, and the extent of such concentration may be suitably selected depending on the amount of the component supplemented or the amount of the bleaching solution or bleach-fixing solution.

The processing time in the bleaching step or bleach-fixing step in which the processing solution of the present invention is employed may preferably be 20 seconds to 10 minutes, more preferably 30 seconds to 7 minutes. The processing temperature may usually be 20° to 50° C.

In the following, the present invention is described by referring to Examples for the purpose illustrating in detail the effect of the invention, but the embodiments of the present invention are not limited at all by these Examples.

EXAMPLE 1

By employment of a layer constitution similar to that adopted for light-sensitive silver halide color photographic material in this field of the art, while permitting various auxiliary layers to exist as intermediate layers, a halation preventive layer, a red-sensitive silver halide emulsion layer, a green-sensitive silver halide emulsion layer and a blue-sensitive silver halide emulsion layer were formed from the side of the support, with a mono-dispersed high sensitivity silver halide emulsion layer being arranged on the outermost side of said blue-sensitive silver halide emulsion layer.

Layer 1 ... Halation preventive layer was provided by coating of a dispersion, which was prepared by dispersing, with 3 g of gelatin, 0.8 g of black colloidal silver exhibiting high absorption of light at wave-length region of 400 to 700 nm obtained by reduction of silver nitrate with the use of hydroquinone as the reducing agent.

Layer 2 ... A low sensitivity red-sensitive silver halide emulsion layer containing 1.5 g of a low sensitivity red-sensitive silver iodobromide emulsion (AgI: 8 mole %), 1.6 g of gelatin and 0.4 g of tricresyl phosphate (hereinafter called TCP) having 0.80 g of 1-hydroxy-4-($\beta$-methoxyethyl-aminocarbonylmethoxy)-N-[$\delta$-(2,4-di-t-amylphenoxy)butyl]-2-naphthoamide [hereinafter called cyan coupler (C-1)] and 0.028 g of 1-hydroxy-4-[4-(1-hydroxy-8-acetamido-3,6-disulfo-2-naphthylazo)phenoxy]-N-[$\delta$-(2,4-di-t-amylphenoxy)-butyl]-2-naphthoamide disodium [hereinafter called colored cyan coupler (CC-1)] dissolved therein.

Layer 3 ... A high sensitivity red-sensitive silver halide emulsion layer containing 1.1 g of a high sensitivity red-sensitive silver iodobromide emulsion (AgI: 7 mole %), 1.2 g of gelatin and 0.15 g of TCP having 0.23 g of the cyan coupler (C-1) and 0.020 g of the colored cyan coupler (CC-1) dissolved therein.

Layer 4 ... An intermediate layer containing 0.04 g of di-n-butylphthalate (hereinafter called DBP) having 0.07 g of 2,5-di-t-octylhydroquinone [hereinafter called antistaining agent (HQ-1)] dissolved therein and 1.2 g of gelatin.

Layer 5 ... A low sensitivity green-sensitive silver halide emulsion layer containing 1.6 g of low sensitivity green-sensitive silver iodobromide emulsion (AgI: 15 mole %), 1.7 g of gelatin and 0.3 g of TCP having three kinds of couplers of 0.30 g of 1-(2,4,6-trichlorophenyl)-3-[3-(2,4-di-t-amylphenoxyacetamido)benzeneamido]-5-pyrazolone [hereinafter called magenta coupler (M-1)], 0.20 g of 4,4-methylene-bis-1 1-(2,4,6-trichlorophenyl)-3-[3-(2,4-di-t-amylphenoxyacetamido)benzeneamido]-5-pyrazolone [hereinafter called magenta coupler (M-2)] and 0.066 g of 1-(2,4,6-trichlorophenyl)-4-(1-naphthylazo)-3-(2-chloro-5-octadecenylsuccinimidoanilino)-5-pyrazolone [hereinafter called colored magenta coupler (CM-1)] dissolved therein.

Layer 6 ... A high sensitivity green-sensitive silver halide emulsion layer containing 1.5 g of a high sensitivity green-sensitive silver iodobromide emulsion (AgI: 11 mole %), 1.9 g of gelatin and 0.12 g of TCP having 0.093 g of the magenta coupler (M-1), 0.094 g of the magenta coupler (M-2) and 0.049 g of the colored magenta coupler (CM-1) dissolved therein.

Layer 7 ... A yellow filter layer containing 0.2 g of yellow colloidal silver, 0.11 g of DBP having 0.2 g of the antistaining agent (HQ-1) dissolved therein and 2.1 g of gelatin.

Layer 8 ... A low sensitivity blue-sensitive silver halide emulsion layer containing 0.95 g of a low sensitivity blue-sensitive silver iodobromide emulsion (AgI: 6 mole %), 1.9 g of gelatin and 0.93 g of DBP having 1.84 g of $\alpha$-[4-(1-benzyl-2-phenyl-3,5-dioxo-1,2,4-triazolizinyl)]-$\alpha$-pivaloyl-2-chloro-5-[$\gamma$-(2,4-di-t-amylphenoxy)butaneamido]acetanilide [hereinafter called yellow coupler (Y-1)] dissolved therein.

Layer 9 ... A high sensitivity blue-sensitive silver halide emulsion layer containing 1.2 g of a high sensitivity mono-dispersed blue-sensitive silver iodobromide emulsion (AgI: 7 mole %), 2.0 g of gelatin and 0.23 g of DBP having 0.46 g of the yellow coupler (Y-1) dissolved therein.

Layer 10 ... A second protective layer comprising gelatin.

Layer 11 ... A first protective layer comprising 2.3 g of gelatin.

The photographic constituent layer of the sample prepared had a dry film thickness of 25 μm. Each sample was processed according to the following processing steps.

| Processing step | Processing temperature | Processing time |
| --- | --- | --- |
| Color developing | 37.8° C. | 3 min. 15 sec. |
| Bleach-fixing | 37.8° C. | 1 min., 3 min. |
| Water washing | 37.8° C. | 2 min. |
| Stabilizing | 37.8° C. | 30 sec. |

Also, the processing solutions prepared according to the following recipes were employed.

| [Color developing solution] | |
| --- | --- |
| Potassium carbonate | 30 g |
| Sodium sulfite | 2.0 g |
| Hydroxyamine sulfate | 2.0 g |
| 1-Hydroxyethylidene-1,1-diphosphonic acid | 1.0 g |
| Potassium bromide | 1.2 g |
| Magnesium chloride | 0.8 g |
| Sodium hydroxide | 3.4 g |
| N—ethyl-N—$\beta$-hydroxyethyl-3-methyl-4-aminoaniline sulfate | 4.6 g |
| (made up to one liter with addition of water and adjusted to pH 10.1 with sodium hydroxide). | |
| [Bleach-fixing solution] | |
| Bleaching agent (added following Table 1) | |
| Chelating agent (added following Table 1) | |
| Ammonium sulfite (50% solution) | 10.0 g |
| Ammonium thiosulfate (70% solution) | 200.0 g |
| (made up to one liter with addition of water and adjusted to pH 75 with ammonium hydroxide). | |
| [Stabilizing solution] | |
| Formalin (35% aqueous solution) | 7.0 ml |
| | 1.0 ml |

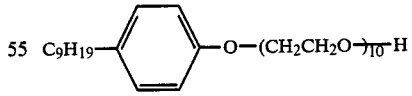

(made up to one liter with addition of water).

TABLE 1

| | | Bleach-fixing solution | Bleaching agent | Amount added (g) | Chelating agent | Amount added (g) | Residual silver amount (mg/dm$^2$) | |
| --- | --- | --- | --- | --- | --- | --- | --- | --- |
| | | | | | | | 1 min. | 3 min. |
| Comparative example | | A | Ferric sodium ethylene- | 60 | Ethylene-diamine- | 5 | 8.1 | 2.3 |

TABLE 1-continued

|  | Bleach-fixing solution | Bleaching agent | Amount added (g) | Chelating agent | Amount added (g) | Residual silver amount (mg/dm$^2$) 1 min. | 3 min. |
|---|---|---|---|---|---|---|---|
|  |  | diamine-tetraacetate |  | tetraacetic acid |  |  |  |
|  | B | Ferric sodium nitrilo-triacetate | 60 | Nitrilo-triacetic acid | 5 | 8.4 | 1.6 |
|  | C | Ferric sodium ethylether diamine-tetraacetate | 60 | None | — | 6.4 | 2.1 |
|  | D | Ferric sodium glycolether diamine-tetraacetate | 60 | None | — | 7.2 | 1.4 |
|  | E | Ferric sodium diamino-propanol-tetraacetate | 60 | None | — | 9.2 | 0.9 |
|  | F | Glycolether-diaminetetra-acetic acid iron complex | 60 | None | — | 6.3 | 1.3 |
|  |  | Ferric ethylene-diaminetetra-acetate | 5 |  |  |  |  |
|  | G | Ethylether-diaminetetra-acetic acid iron complex | 60 | None | — | 8.6 | 0.87 |
|  |  | Nitrilo-triacetic acid | 5 |  |  |  |  |
|  | H | Ferric sodium glycolether diamine-tetraacetate | 60 | Ethylene-diamine-tetraacetic acid | 5 | 7.1 | 0.96 |
|  | I | Ferric sodium diamino-propanol-tetraacetate | 60 | Ferric sodium diethylene triamine-pentaacetate | 5 | 6.2 | 1.2 |
| This invention | J | Ferric complex of Exemplary compound (A - 1) | 60 | None | — | 0.64 | 0 |
|  | K | Ferric complex of Exemplary compound (A - 2) | 60 | None | — | 0.39 | 0 |
|  | L | Ferric complex of Exemplary compound (A - 4) | 60 | Exemplary compound (A - 4) | 5 | 0.68 | 0 |
|  | M | Ferric complex of Exemplary compound (A - 5) | 60 | None | — | 0.90 | 0 |
|  | N | Ferric complex of Exemplary compound (A - 6) | 60 | None | — | 0.87 | 0 |
|  | O | Ferric complex of Exemplary compound (A - 7) | 60 | Exemplary compound (A - 7) | 5 | 0.34 | 0 |
|  | P | Ferric complex of Exemplary compound (A - 10) | 60 | Exemplary compound (A - 10) | 5 | 0.56 | 0 |
|  | Q | Ferric complex of Exemplary compound (B - 4) | 60 | None | — | 0 | 0 |

As is apparent from the results in Table 1, the bleach-fixing solution containing the metal complex of large cyclic polyamine derivative of the present invention can bleach-fix the image silver within a shorter time as compared with the bleach-fixing solutions for comparative purpose, thus having excellent bleach-fixing ability. Also, the samples processed with the bleach-fixing solution of the present invention was free from stain and also without generation of complex color badness.

EXAMPLE 2

The samples of Example 1 were subjected to stepwise exposure at a color temperature of 4900 K. by the tungsten light source used through a filter, and the following processings (a), (b), (c) and (d) were conducted, and the residual silver in the light sensitive materials were examined in the same manner as in Example 1.

Processing (a):

| [Processing step] | [Temperature] | [Time] |
|---|---|---|
| Color developing | 38° C. | 3 min. 15 sec. |
| Bleaching | 38° C. | 30 sec., 1 min. 40 sec. |
| Water washing | 38° C. | 2 min. |
| Fixing | 38° C. | 4 min. 20 sec. |
| Water washing | 38° C. | 4 min. |
| Stabilizing | 38° C. | 1 min. |
| Drying | 50° C. | — |

The processing solutions employed in the respective processing steps had the following compositions.

Color developing solution:
| | |
|---|---|
| 4-Amino-3-methyl-N—ethyl-N—(β-hydroxyethyl)-aniline sulfate | 4.8 g |
| Anhydrous sodium sulfite | 0.14 g |
| Hydroxylamine ½ sulfate | 1.98 g |
| Sulfuric acid | 0.74 g |
| Anhydrous potassium carbonate | 28.85 g |
| Anhydrous potassium hydrogen carbonate | 1.16 g |
| Anhydrous potassium sulfite | 5.10 g |
| Potassium bromide | 1.16 g |
| Sodium chloride | 0.14 g |
| Trisodium nitrilotriacetate (monohydrate) | 1.20 g |
| Potassium hydroxide | 1.48 g |

(made up to one liter with addition of water).

Bleaching solution:
| | |
|---|---|
| Bleaching agent (added in amounts shown in Table 2) | |
| Chelating agent (added in amounts shown in Table 2) | |
| Ammonium bromide | 150.0 g |
| Glacial acetic acid | 10.0 g |

(made up to one liter with addition of water, and adjusted to pH 6.0 with ammonia water).

Fixing solution:
| | |
|---|---|
| Ammonium thiosulfate | 175.0 g |
| Anhydrous sodium sulfite | 8.6 g |
| Sodium metasulfite | 2.3 g |

(made up to one liter with addition of water, and adjusted to pH 6.0 with acetic acid).

Stabilizing solution:
| | |
|---|---|
| Formalin | 6.0 ml |
| Konidax (produced by Konishiroku Photo Industry Co., Ltd.) | 7.5 ml |

(made up to one liter with addition of water).

TABLE 2

| | Bleaching solution | Bleaching agent | Amount added (g) | Chelating agent | Amount added (g) | Residual silver amount (mg/dm$^2$) 30 sec. | 1 min. 40 sec. |
|---|---|---|---|---|---|---|---|
| Comparative example | A | Ferric sodium ethylenediaminetetraacetate | 60 | Ethylenediaminetetraacetic acid | 5 | 16 | 2.2 |
| | B | Ferric sodium nitrilotriacetate | 60 | Nitrilotriacetic acid | 5 | 14 | 4.1 |
| | C | Ferric sodium ethyletherdiaminetetraacetate | 60 | None | — | 18 | 3.2 |
| | D | Ferric sodium glycoletherdiaminetetraacetate | 60 | None | — | 17 | 4.6 |
| | E | Ferric sodium diaminopropanoltetraacetate | 60 | None | — | 14 | 2.8 |
| | F | Glycoletherdiaminetetraacetic acid iron complex | 60 | None | — | 12 | 3.2 |
| | | Ferric ethylenediaminetetraacetate | 5 | | | | |
| | G | Ethyletherdiaminetetraacetic acid iron complex | 60 | None | — | 11 | 2.6 |
| | | Nitrilotriacetic acid | 5 | | | | |
| | H | Ferric sodium glycoletherdiaminetetraacetate | 60 | Ethylenediaminetetraacetic acid | 5 | 16 | 2.8 |
| | I | Ferric sodium diaminopropanoltetraacetate | 60 | Ferric sodium diethylenetriaminepentaacetate | 5 | 11 | 3.1 |
| This invention | J | Ferric complex of Exemplary compound (A - 1) | 100 | Exemplary compound (A - 1) | 5 | 2.1 | 0 |
| | K | Ferric complex of Exemplary compound (A - 2) | 100 | Exemplary compound (A - 2) | 5 | 1.4 | 0 |
| | L | Ferric complex of Exemplary compound (A - 4) | 100 | Exemplary compound (A - 4) | 5 | 2.0 | 0 |

TABLE 2-continued

| Bleaching solution | Bleaching agent | Amount added (g) | Chelating agent | Amount added (g) | Residual silver amount (mg/dm$^2$) 30 sec. | 1 min. 40 sec. |
|---|---|---|---|---|---|---|
| M | Ferric complex of Exemplary compound (A - 5) | 100 | None | — | 1.3 | 0 |
| N | Ferric complex of Exemplary compound (A - 6) | 100 | None | — | 2.1 | 0 |
| O | Ferric complex of Exemplary compound (A - 7) | 100 | None | — | 1.2 | 0 |
| P | Ferric complex of Exemplary compound (A - 10) | 100 | None | — | 1.4 | 0 |
| Q | Ferric complex of Exemplary compound (B - 4) | 100 (B - 4) | Exemplary compound | 5 | 1.6 | 0 |

As is apparent from Table 2, the bleaching solution of the present invention has more excellent bleaching power as compared with those of comparative examples.

EXAMPLE 3

For observation of storability and tar generation of the processing solution of the present invention, a bleach-fixing solution containing a color developing solution was prepared.

Bleach-fixing solution:

| | |
|---|---|
| Bleaching agent (added following Table 3) | |
| Chelating agent (added following Table 3) | |
| Color developing solution | 300 ml |
| 60% aqueous ammonium thiosulfate | 120 ml |
| 40% aqueous ammonium sulfite | 22 ml |
| (adjusted to pH 7.0 with glacial acetic acid or ammonium hydroxide). | |

The color developing solution used in the bleach-fixing solution had the following composition.

| (Color developing solution) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| Color developing agent (N—ethyl-N—β-methanesulfonamidoethyl-3-methyl-4-aminoaniline sulfate) | 6.0 g |
| Fluorescent brightening agent (4,4'-diaminostilbenesulfonic acid derivative) | 1.0 g |
| Potassium hydroxide | 2.0 g |
| (made up to one liter with addition of water, and adjusted to pH 10.20). | |

The processing solution prepared was filled in a narrow mouth 500 ml glass bottle up to the mouth, and stored at 38° C. for 4 weeks.

Four weeks later, the sulfites were quantitatively determined by iodine titration.

Further, the processing solution was left to stand for 4 weeks and the extent of tar generation was observed to obtain the results shown in Table 3.

TABLE 3

| | Sample No. | Bleaching agent (metal complex) | Chelating agent | Concentration of (NH$_4$)$_2$SO$_4$ in bleach-fixing solution after 4 weeks | Tar generation after 8 weeks |
|---|---|---|---|---|---|
| Comparative example | 1 | EDTA Fe$^{III}$ | EDTA (Ethylenediaminetetraacetic acid) | 0.25 | much |
| Comparative example | 2 | IDA Fe$^{III}$ | IDA (Iminodiacetic) acid) | 0.42 | much |
| Comparative example | 3 | M-EDTA Fe$^{III}$ | M-EDTA (1,2-Propylenediaminetetraacetic acid) | 0.61 | much |
| Comparative example | 4 | M-IDA Fe$^{III}$ | Me-IDA (Methyl(iminodiacetic acid) | 0.61 | much |
| Comparative example | 5 | DTPA Fe$^{III}$ | DTPA (DIETHYL-enetriaminapentaacetic acid) | 1.36 | much |
| Comparative example | 6 | Cy-DTA Fe$^{III}$ | Cy-DTA (trnas-cyclohexanediaminetetraacetic acid) | 1.10 | much |
| Comparative example | 7 | G-EDTA Fe$^{III}$ | G-EDTA (Glycoletherdiaminetetraacetic acid) | 0.84 | much |

TABLE 3-continued

| Sample No. | Bleaching agent (metal complex) | Chelating agent | Concentration of $(NH_4)_2SO_4$ in bleach-fixing solution after 4 weeks | Tar generation after 8 weeks |
|---|---|---|---|---|
| This invention 8 | Ferric complex of Exemplary compound (A - 3) | | 6.0 | None |
| This invention 9 | Ferric complex of Exemplary compound (A - 4) | | 8.2 | None |
| This invention 10 | Ferric complex of Exemplary compound (A - 10) | | 8.1 | None |
| This invention 11 | Ferric complex of Exemplary compound (B - 4) | | 7.1 | None |

As is apparent from Table 3, the bleach-fixing solutions for comparative purpose are rapid in reduction speed of the sulfites in said solution, thus being poor in storability, and silver sulfide or sulfur is liable to be generated. Also, generation of tar also readily occurs. In contrast, it can be appreciated that the bleach-fixing solutions of the present invention exhibit little reduction of the sulfites, have excellent storage stability without generation of tar, thus being excellent processing solutions.

We claim:

1. A processing solution having bleaching ability for use in processing light-sensitive silver halide color photographic material, which comprises a color developing agent and an effective amount of at least one bleaching agent selected from the group consisting of metal complexes of large cyclic polyamine derivatives with the sum of the atoms for forming the ring being at least nine.

2. The processing solution according to claim 1, wherein said metal complex of large cyclic polyamine derivative comprises a large cyclic polyamine derivative comprising a compound having at least three nitrogen atoms linked through at least two carbon atoms to form a ring and a metal.

3. The processing solution according to claim 2, wherein said large cyclic polyamine derivative is one having at least 3 nitrogen atoms for forming said ring with the sum of the atoms for forming the ring being at least 9.

4. The processing solution according to claim 3, wherein said large cyclic polyamine derivative is at least one selected from the group consisting of the compounds represented by the formulae (I) to (XVI):

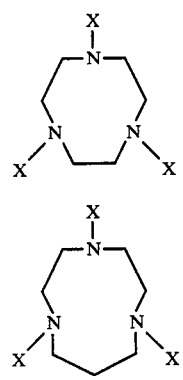
(I)

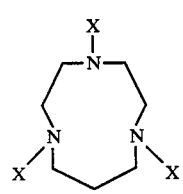
(II)

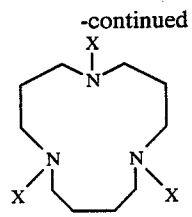
(III)

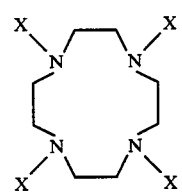
(IV)

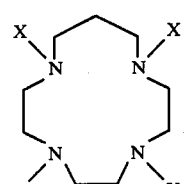
(V)

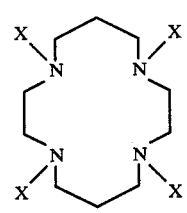
(VI)

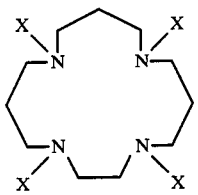
(VII)

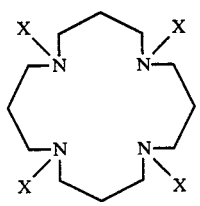
(VIII)

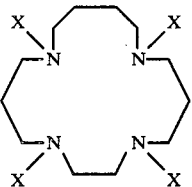 (IX)

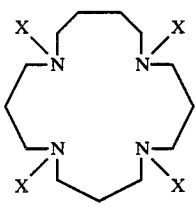 (X)

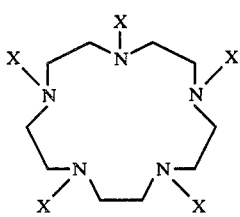 (XI)

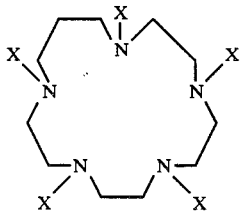 (XII)

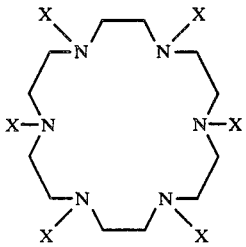 (XIII)

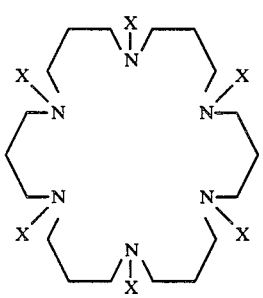 (XIV)

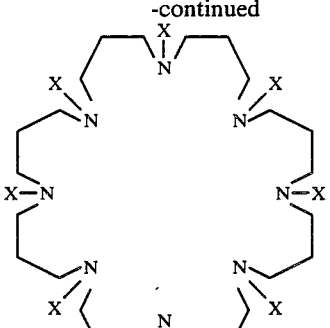 (XV)

and

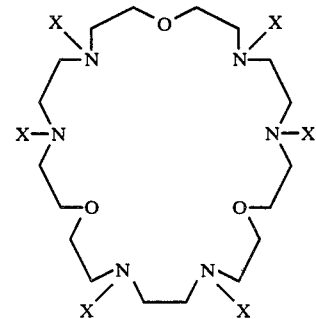 (XVI)

wherein X represents a hydrogen atom, a carboxymethyl group or a phosphonomethyl group.

5. The processing solution according to claim 1, wherein said metal complex of large cyclic polyamine derivative is used in an amount of from 3 g to 350 g per liter of the processing solution.

6. The processing solution according to claim 2, wherein said metal is selected from the group consisting of iron, copper and cobalt.

7. The processing solution according to claim 2, wherein said metal is selected from the group consisting of iron, copper and cobalt, and said metal complex of large cyclic polyamine derivative is used in an amount of from 3 g to 350 g per liter of the processing solution.

8. The processing solution according to claim 3, wherein said metal is selected from the group consisting of iron, copper and cobalt, and said metal complex of large cyclic polyamine derivative is used in an amount of from 3 g to 350 g per liter of the processing solution.

9. The processing solution according to claim 4, wherein said metal is selected from the group consisting of iron, copper and cobalt, and said metal complex of large cyclic polyamine derivative is used in an amount of from 3 g to 350 g per liter of the processing solution.

10. The processing solution according to claim 9, wherein said metal complex is a ferric complex.

11. The processing solution according to claim 8, wherein said ring contains at least one substituent selected from the group consisting of carboxymethyl and phosphonomethyl.

12. The processing solution according to claim 9, wherein said ring contains at least one substituent selected from the group consisting of carboxymethyl and phosphonomethyl.

13. The processing solution according to claim 11, wherein said metal complex is a ferric complex.

14. The processing solution according to claim 12, wherein said metal complex is a ferric complex.

* * * * *